(12) United States Patent
Maienfisch et al.

(10) Patent No.: US 6,566,518 B1
(45) Date of Patent: May 20, 2003

(54) TRIFLUOROMETHYLPYRI(MI)DINE CARBOXAMIDES

(75) Inventors: Peter Maienfisch, Rodersdorf (CH); Saleem Farooq, Arisdorf (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 10/031,914

(22) PCT Filed: Jul. 28, 2000

(86) PCT No.: PCT/EP00/07312

§ 371 (c)(1),
(2), (4) Date: Jan. 18, 2002

(87) PCT Pub. No.: WO01/09104

PCT Pub. Date: Feb. 8, 2001

(30) Foreign Application Priority Data

Jul. 30, 1999 (CH) .............................................. 1407/99

(51) Int. Cl.[7] ................... C07D 239/28; C07D 213/78; A01N 43/54; A01N 43/40
(52) U.S. Cl. ........................ 544/335; 546/316; 514/256; 514/357
(58) Field of Search .......................... 546/316; 544/335; 514/256, 357

(56) References Cited

U.S. PATENT DOCUMENTS 3,541,106 A 11/1970 Krenzer et al. .......... 260/295.5

FOREIGN PATENT DOCUMENTS

EP 0569912 A1 5/1993

*Primary Examiner*—Venkataraman Balasubramanian
(74) *Attorney, Agent, or Firm*—Rose M. Allen

(57) ABSTRACT

Compounds of formula

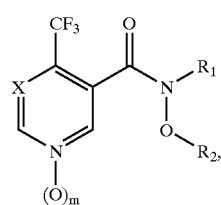

(I)

are described, along with a method of producing pesticidal compositions and the use of these compounds as pesticides.

7 Claims, No Drawings

TRIFLUOROMETHYLPYRI(MI)DINE CARBOXAMIDES

The object of the present invention is a compound of the formula

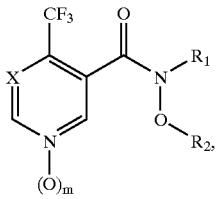

(I)

wherein $R_1$ and $R_2$, independently of one another, are hydrogen, $C_1$–$C_6$-alkyl, $C_3$–$C_8$-cycloalkyl, $C_2$–$C_{20}$-alkenyl or $C_3$–$C_{20}$-alkinyl; or mono- or poly-substituted $C_1$–$C_{20}$-alkyl, $C_2$–$C_{20}$-alkenyl or $C_3$–$C_{20}$-alkinyl;

aryl or heterocyclyl, or aryl or heterocyclyl which are substituted by one or more substituents selected from the group consisting of $C_1$–$C_6$-alkyl, halogen-$C_1$–$C_6$-alkyl, $C_2$–$C_6$-alkenyl, $C_3$–$C_6$-alkinyl, halogen, $C_1$–$C_6$-alkoxy, halogen-$C_1$–$C_6$-alkoxy, nitro, cyano, $C_3$–$C_8$-cycloalkyl, halogen-$C_3$–$C_8$-cycloalkyl, $C_3$–$C_6$-alkenyloxy, $C_1$–$C_4$-alkylthio and di-($C_1$–$C_4$-alkyl)amine;

or —C(=O)—$R_3$;

$R_3$ is hydrogen, OH, SH, $C_1$–$C_6$-alkyl, $C_3$–$C_8$-cycloalkyl, $C_1$–$C_6$-alkoxy, $C_1$–$C_6$-alkylthio, $C_2$–$C_6$-alkenyl, $C_3$–$C_6$-alkenyloxy, $C_3$–$C_6$-alkinyl, $C_3$–$C_6$-alkinyloxy, di-($C_1$–$C_4$-alkyl)amine, aryl, heterocyclyl, aryloxy, benzyloxy or heterocyclyloxy;

$C_1$–$C_6$-alkyl, $C_3$–$C_8$-cycloalkyl, $C_1$–$C_6$-alkoxy, $C_1$–$C_6$-alkylthio, $C_3$–$C_6$-alkenyl, $C_3$–$C_6$-al-kenyloxy, $C_3$–$C_6$-alkinyl or $C_3$–$C_6$-alkinyloxy, which are substituted by one or more substituents selected from the group consisting of halogen, nitro, cyano, —OH, —SH, $C_3$–$C_8$-cycloalkyl, halogen-$C_3$–$C_8$-cycloalkyl and di-($C_1$–$C_4$-alkyl)amine;

or aryl, heterocyclyl, aryloxy, benzyloxy or heterocyclyloxy, which are optionally substituted by one to three substituents selected from the group consisting of halogen, nitro, cyano, —OH, —SH, COOH, COH, $C_1$–$C_6$-alkyl, $C_1$–$C_6$-alkoxy, $C_1$–$C_6$-alkylthio, halogen-$C_1$–$C_6$-alkyl, halogen-$C_1$–$C_6$-alkoxy, halogen-$C_1$–$C_6$-alkylthio, $C_3$–$C_8$-cycloalkyl, halogen-$C_3$–$C_8$-cycloalkyl and di-($C_1$–$C_4$-alkyl)amine;

m is 0 or 1; and

X is CH or N;

and the compounds thereof, and where appropriate to E/Z isomers, to mixtures of E/Z isomers and/or to tautomers, in each case in free form or in salt form;

a method of producing and the use of these compounds, pesticides whose active ingredient is selected from these compounds or from an agrochemically employable salt thereof, a method of producing and the use of these compositions, plant propagating material that has been treated with these compositions and a method of controlling pests.

In literature, certain pyridine derivatives have been proposed as active ingredients in pesticides. The biological properties of these known compounds, however, are not fully satisfactory in the field of pest control, which is why there is a need to produce further compounds with pesticidal properties, especially for the control of insects and members of the order Acarina; this problem is solved according to the invention with the development of the present compounds of formula (I).

The compounds of formula (I) may be present partly in the form of tautomers. Accordingly, any reference to compounds of formula (I) hereinbefore and hereinafter is understood to include also their corresponding tautomers, even if the latter are not specifically mentioned in each case.

The compounds of formula (I) and where appropriate their tautomers can form salts, for example acid addition salts. These are formed for example with strong inorganic acids, typically mineral acids, e.g. sulphuric acid, a phosphoric acid or a hydrohalic acid, or with strong organic carboxylic acids, typically $C_1$–$C_4$alkanecarboxylic acids substituted where appropriate for example by halogen, e.g. acetic acid, such as optionally unsaturated dicarboxylic acids, e.g. oxalic, malonic, maleic, fumaric or phthalic acid, such as hydroxycarboxylic acids, e.g. ascorbic, lactic, malic, tartaric or citric acid, or benzoic acid, or with organic sulphonic acids, typically $C_1$–$C_4$alkane or arylsulphonic acids substituted where appropriate for example by halogen, e.g. methane- or p-toluene-sulphonic acid. In a broader sense, compounds of formula (I) with at least one acid group can form salts with bases. Suitable salts with bases are for example metal salts, such as alkali or alkaline earth metal salts, e.g. sodium, potassium or magnesium salts, or salts with ammonia or an organic amine, such as morpholine, piperidine, pyrrolidine, a mono-, di- or tri-lower alkylamine, e.g. ethyl, diethyl, triethyl or dimethylpropylamine, or a mono-, di- or trihydroxy-lower alkylamine, e.g. mono-, di- or triethanolamine. Corresponding internal salts where appropriate may also be formed. The free form is preferred. Of the salts of compounds of formula (I), the agrochemically beneficial salts are preferred. Hereinbefore and hereinafter, the free compounds of formula (I) or their salts are understood where appropriate to include also the corresponding salts, or the salts are understood to include also the free compounds of formula (I). The same applies to tautomer of compounds of formula (I) and salts thereof.

Unless otherwise defined, the general terms used hereinabove and hereinbelow have the meanings given hereinbelow.

Halogen—as a group per se or as structural element of other groups and compounds such as haloalkyl, halocycloalkyl, haloalkenyl, haloalkinyl and haloalkoxy—is fluorine, chlorine, bromine or iodine, in particular fluorine, chlorine or bromine, mainly fluorine or chlorine, especially chlorine.

If not otherwise defined, carbon-containing groups and compounds each contain 1 to 20, inclusively, preferably 1 to 18, in particular 1 to 10, especially 1 to 6, in particular 1 to 4, especially 1 to 3, particularly 1 or 2, carbon atoms, with methyl being preferred in particular.

Alkyl—as a group per se and as structural element of other groups and compounds such as haloalkyl, alkoxy, alkoxyalkyl, haloalkoxy, alkoxycarbonyl, alkylthio, haloalkylthio, alkylsulphonyl and alkylsulphonyloxy—is, in each case with due consideration of the specific number of carbon atoms in the group or compound in question, —either straight-chained, e.g. methyl, ethyl, n-propyl, n-butyl, n-hexyl, n-octyl, n-decyl, n-dodecyl, n-hexadecyl or n-octadecyl, or branched, for example isopropyl, isobutyl, sec-butyl, tert-butyl, isopentyl, neopentyl or isohexyl.

Alkenyl and alkinyl—as groups per se and as structural elements of other groups and compounds, such as of haloalkenyl, haloalkinyl, alkenyloxy, haloalkenyloxy, alkinyloxy or halo-alkinyloxy—are straight-chained or branched and respectively contain two or preferably one unsaturated carbon-carbon bond(s). Vinyl, prop-2-en-1-yl, 2-methylprop-2-en-1-yl, but-2-en-1-yl, but-3-en-1-yl, prop-2-in-1-yl, but-2-in-1-yl and but-3-in-1-yl may be example.

Cycloalkyl—as a group per se and as a structural element of other groups and compounds, for example of alkyl—is cyclopropyl, cyclobutyl, cyclopentyl, cyclohexyl, cycloheptyl and cyclooctyl. Cyclopentyl and cyclohexyl are preferred, in particular cyclopropyl.

Halogen-substituted carbon-containing groups and compounds, such as haloalkyl and haloalkoxy, can be partially halogenated or perhalogenated, in the case of polyhalogenation it being possible for the halogen substituents to be identical or different. Examples of haloalkyl—as a group per se and as structural element of other groups and compounds such as haloalkoxy, —are methyl which is mono- to trisubstituted by fluorine, chlorine and/or bromine, such as $CHF_2$, $CF_3$ or $CH_2Cl$; ethyl which is mono- to pentasubstituted by fluorine, chlorine and/or bromine, such as $CH_2CF_3$, $CF_2CF_3$, $CF_2CCl_3$, $CF_2CHCl_2$, $CF_2CHF_2$, $CF_2CFCl_2$, $CH_2CH_2Cl$, $CF_2CHBr_2$, $CF_2CHClF$, $CF_2CHBrF$ oder $CClFCHClF$; propyl or isopropyl, mono- to heptasubstituted by fluorine, chlorine and/or bromine, such as $CH_2CHBrCH_2Br$, $CF_2CHFCF_3$, $CH_2CF_2CF_3$, $CF_2CF_2CF_3$, $CH(CF_3)_2$ or $CH_2CH_2CH_2Cl$; and butyl or one of its isomers, mono- to nonasubstituted by fluorine, chlorine and/or bromine, such as $CF(CF_3)CHFCF_3$, $CF_2(CF_2)_2CF_3$ oder $CH_2(CF_2)_2CF_3$.

In di-($C_1$–$C_4$-alkyl)amine, the two alkyl groups are independent of each other.

Aryl preferably signifies phenyl or naphthyl, especially phenyl.

Heterocyclyl signifies a 5- to 7-membered, saturated or unsaturated, preferably aromatic ring with one to three hetero atoms selected from the group consisting of N, O and S. Preference is given to aromatic 5- and 6-rings that have one nitrogen atom as a hetero atom and optionally one further hetero atom, preferably nitrogen or sulphur, especially nitrogen. Preferred heteroaryl radicals are -pyrazinyl, -pyrid-3-yl, -pyrid-2-yl, -pyrid-4-yl, -pyrimidine-2-yl, -pyrimidine-4-yl, -pyrimidine-5-yl, -thiazol-2-yl, -oxazol-2-yl, -furan-2-yl, -furan-3-yl, -tetrahydrofuran-3-yl, -thien-2-yl, -thien-3-yl, thiazol-5-yl and -thiazol-2-yl, especially -pyrid-3-yl, and thiazol-5-yl.

Depending on the substitution possibilities on the heterocyclyl radical, aryl and heterocyclyl radicals may bear one to three, preferably one, substituent selected from the group consisting of $C_1$–$C_6$-alkyl, $C_2$–$C_6$-alkenyl, $C_3$–$C_6$-alkinyl; halogen, nitro, cyano, —OH, —SH, $C_3$–$C_8$-cycloalkyl, halogen-$C_3$–$C_8$-cycloalkyl, $C_1C_6$-alkoxy, halogen-$C_1$–$C_6$-alkoxy, $C_3$–$C_6$-alkenyloxy, $C_1$–$C_4$-alkylthio and di-($C_1$–$C_4$-alkyl)amine. Unsubstituted aryl and heterocyclyl radicals are preferred. Also preferred are aryl and heterocyclyl bearing one substituent, especially chlorine.

Preferred embodiments in terms of the invention are (1) compounds of formula (I), wherein $R_1$ is hydrogen, $C_1$–$C_4$-alkyl, $C_3$–$C_8$-cycloalkyl, $C_3$–$C_6$-alkenyl, $C_3$–$C_6$-alkinyl; or $C_1$–$C_6$-alkyl, $C_3$–$C_6$-alkenyl or $C_3$–$C_6$-alkinyl, which are substituted by one or more substituents selected from the group consisting of halogen, nitro, cyano, —OH, —SH, $C_3$–$C_8$-cycloalkyl, halogen-$C_3$–$C_8$-cycloalkyl, $C_1$–$C_6$-alkoxy, halogen-$C_1$–$C_6$-alkoxy, $C_3$–$C_6$-alkenyloxy, $C_1$–$C_4$-alkylthio, di-($C_1$–$C_4$-alkyl)amine, —C(=O)—$R_4$ (wherein $R_4$ has the same significance as given above for $R_3$), aryl, aryloxy, arylthio, heterocyclyl or heterocyclyloxy; or aryl or heterocyclyl, which are optionally substituted by one or more substituents selected from the group consisting of $C_1$–$C_6$-alkyl, halogen-$C_1$–$C_6$-alkyl, halogen, $C_1$–$C_6$-alkoxy, halogen-$C_1$–$C_6$-alkoxy, nitro, cyano, $C_3$–$C_8$-cycloalkyl and di-($C_1$–$C_4$-alkyl)amine;

especially by halogen, nitro, cyano, $C_3$–$C_8$-cycloalkyl, $C_1$–$C_6$-alkoxy, di-($C_1$–$C_4$-alkyl)amine, —C(=O)—$R_4$ (wherein $R_4$ has the same significance as given above for $R_3$), aryl or heterocyclyl; or aryl or heteroaryl, which are optionally substituted by one or more substituents selected from the group consisting of $C_1$–$C_2$-alkyl, halogenmethyl, halogen, $C_1$–$C_6$-alkoxy, halogen, $C_1$–$C_2$-alkoxy, nitro, cyano, $C_3$–$C_6$-cycloalkyl and di-($C_1$–$C_4$-alkyl)amine;

or —C(=O)—$R_3$;

especially wherein $R_1$ is hydrogen, $C_1$–$C_3$-alkyl, $C_3$–$C_6$-cycloalkyl, $C_3$–$C_4$-alkenyl, $C_3$–$C_4$-alkinyl; or $C_1$–$C_2$-alkyl, which are substituted by a substituent selected from the group consisting of cyano and di-($C_1$–$C_4$-alkyl)amine, —C(=O)—$R_4$ (wherein $R_4$ has the same significance as given above for $R_3$), aryl or heterocyclyl; or aryl or heteroaryl, which are optionally substituted by one or more substituents selected from the group consisting of $C_1$–$C_2$-alkyl, halogen, $C_1$–$C_2$-alkoxy, halogen-$C_1$–$C_2$-alkoxy, nitro, cyano, $C_3$–$C_5$-cycloalkyl and di-($C_1$–$C_2$-alkyl)amine; or —C(=O)—$R_3$;

in particular wherein $R_1$ is hydrogen, $C_1$–$C_3$-alkyl, cyclohexyl, $C_3$-alkenyl, $C_3$-alkinyl; phenyl, which is optionally mono- or disubstituted by halogen, especially chlorine; benzyl which is optionally monosubstituted by halogen, especially chlorine;

(2) compounds according to item (1) of formula (I), wherein $R_2$ is hydrogen, $C_1$–$C_6$-alkyl, $C_3$–$C_6$-alkenyl, $C_3$–$C_6$-alkinyl; $C_1$–$C_6$-alkyl, which is mono- to trisubstituted by substituents selected from the group consisting of halogen, cyano, $C_1$–$C_2$-alkoxy, halogen-$C_1$–$C_2$-alkoxy, di-($C_1$–$C_2$-alkyl)amine, —C(=O)—$R_4$ (wherein $R_4$ has the same significance as given above for $R_3$), and aryl;

aryl or pyridyl, which are optionally mono- to pentasubstituted by substituents selected from the group consisting of $C_1$–$C_2$-alkyl, halogen-$C_1$–$C_2$-alkyl, halogen, $C_1$–$C_2$-alkoxy, nitro and halogen-$C_1$–$C_2$-alkoxy; or —C(=O)—$R_4$;

especially wherein $R_2$ is hydrogen, $C_1$–$C_2$-alkyl, $C_3$–$C_4$-alkenyl, $C_3$–$C_4$-alkinyl; $C_1$–$C_2$-alkyl, which is mono- to trisubstituted by substituents selected from the group consisting of halogen, cyano, di-($C_1$–$C_2$-alkyl)amine, —C(=O)—$R_4$ and aryl;

aryl or pyridyl, which are optionally substituted by a substituent selected from the group consisting of halogen and nitro; or —C(=O)—$C_1$–$C_4$-Alkyl or —C(=O)-phenyl;

(3) compounds according to item (1) or (2) of formula (I), wherein $R_3$ is hydrogen, OH, $C_1$–$C_2$-alkyl, halogen- $C_1$–$C_2$-alkyl, $C_3$–$C_6$-cycloalkyl, $C_1$–$C_2$-alkoxy, halogen-$C_1$–$C_2$-alkoxy, di-($C_1$–$C_4$-alkyl)amine or aryl, which is optionally mono- to trisubstituted by substituents selected from the group consisting of halogen, nitro, cyano, $C_1$–$C_2$-alkyl, $C_1$–$C_6$-alkoxy and halogen-$C_1$–$C_6$-alkoxy; especially $C_1$–$C_2$-alkyl or aryl, which is optionally substituted by a substituent selected from the group consisting of halogen and $C_1$–$C_2$-alkyl;

(4) compounds according to any of the items (1) to (3) of formula (I), wherein $R_4$ is hydrogen, OH, $C_1$–$C_2$-alkyl, $C_1$–$C_2$-alkoxy, halogen-$C_1$–$C_2$-alkoxy, di-($C_1$–$C_4$-alkyl)amine, aryl, aryloxy, benzyloxy or heterocyclyloxy; especially hydrogen, OH, $C_1$–$C_2$-alkyl, $C_1$–$C_2$-alkoxy, di-($C_1$–$C_4$-alkyl)amine or phenyl;

(5) compounds according to any of the items (1) to (4) of formula (I), wherein X is CH;

(6) compounds according to any of the items (1) to (5) of formula (I), wherein m is 0.

Particularly preferred in terms of the invention are the compounds of formula (I) listed in Tables 1 and 2.

A further object of the invention is the method of preparing the compounds of formula (I), in which m is 0, or a salt thereof, whereby (a) a compound of formula

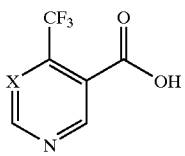

(II)

wherein X is defined as given for formula (I), is reacted with a halogenation agent, if desired in an inert solvent, to form a compound of formula

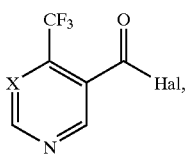

(III)

wherein X is defined as given for formula (I) and Hal is a halogen atom, preferably chlorine or bromine; and (b) this compound of formula (III) is reacted with a compound of the formula

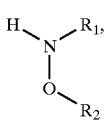

(IV)

wherein $R_1$ and $R_2$ are defined as given for formula (I);

(c) in order to produce a compound of formula (I), in which m is 1, a compound of formula (I) in which m is 0 is reacted with an oxidation agent, for example inorganic peroxides, such as sodium perborate, potassium bichromate, potassium permanganate or hydrogen peroxide; or with an organic per acids, such as perbenzoic acid or peracetic acid, or mixtures of organic acids and hydrogen peroxide, e.g. acetic acid/hydrogen peroxide;

(d) a compound of formula

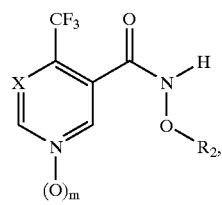

(Ia)

wherein X, m and $R_2$ are defined as given for formula (I), is reacted with a compound of formula $$R_1-Y \qquad (V),$$

wherein $R_1$ is defined as given for formula (I) apart from H, and Y is a leaving group; or (e) a compound of formula

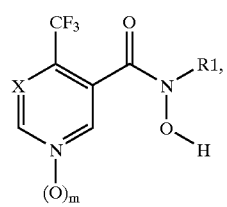

(Ib)

wherein X, m and $R_1$ are defined as given for formula (I), is reacted with a compound of formula $$R_2-Y \qquad (VI),$$

wherein $R_2$ is defined as given for formula (I) apart from H, and Y is a leaving group;

and/or, if so desired, a compound of formula (I) obtainable according to the method or by other means, present in free form or in the form of a salt, is converted into a different compound of formula (I), a mixture of isomers obtainable according to the method is separated and the desired isomer is isolated and/or a free compound of formula (I) obtainable according to the method or by other means is converted into a salt, or a salt of a compound of formula (I) obtainable according to the method or by other means is converted into the free compound of formula (I) or into a different salt.

The starting materials of formulae (II), (III), (IV), (V) and (VI) listed hereinbefore and hereinafter, which are used to produce the compounds of formula (I), in free form or in salt form, are known or may be produced by methods known per se.

The reactions described hereinbefore and hereinafter are carried out in a known manner, e.g. in the absence or, where appropriate, in the presence of a suitable solvent or diluent or a mixture thereof, proceeding as required under conditions of cooling, of ambient temperature, or of heating, e.g. in a temperature range of about −80° C. to the boiling temperature of the reaction medium, preferably about −20° C. to about +150° C., and where appropriate in a closed vessel, under pressure, in an inert gas atmosphere, and/or under non-aqueous conditions. Especially advantageous reaction conditions are described in the examples.

A leaving group is understood to be hereinbefore and hereinafter all the removable groups that are usual in chemical reactions and are known to the person skilled in the art; in particular halogens such as fluorine, chlorine, bromine, iodine, —O—C(=O)—A, —O—P(=O)(—A)$_2$, —O—Si (C$_1$–C$_8$-alkyl)$_3$, —O—(C$_1$–C$_8$-alkyl), —O-aryl, —O—S (=O)$_2$A, —S—P(=O)(—A)$_2$, —S—P(=S)(—A)$_2$, —S—S—(C$_1$–C$_8$-Alkyl), —S—S-aryl, —S—(C$_1$–C$_8$-alkyl), —S-aryl, —S(=O)A, or —S(=O)$_2$A, wherein A is optionally substituted C$_1$–C$_8$-alkyl, C$_2$–C$_8$-alkenyl, C$_2$–C$_8$-alkinyl, optionally substituted aryl, optionally substituted benzyl, C$_1$–C$_8$-alkoxy or di-(C$_1$–C$_8$-alkyl)amine, in which the alkyl groups are independent of one another; NO$_3$, NO$_2$ or sulphate, sulphite, phosphate, phosphite, carboxylate, imino ester, N$_2$ or carbamate. Especially preferred leaving groups are listed under the individual processes.

Process variant (a): The acid halides of formula (III) may be obtained in the usual manner by a reaction with halogenation agents from compounds of formula (II). Suitable halogenation agents are, for example, chlorine, bromine, iodine, oxalyl chloride, POCl$_3$, PCl$_3$, PCl$_5$, SO$_2$Cl$_2$ or SO$_2$Br$_2$, preferably chlorine, bromine or SO$_2$Cl$_2$, Javelle water, poly-sulphur dichloride or sulphur dichloride, especially SOCl$_2$, oxalyl chloride, PCl$_3$, POCl$_3$ or PCl$_5$. The process is generally carried out at temperatures of between −20° C. and +120° C., preferably between 0° C. and +100° C. The reaction may be effected without solvents or in admixture with an inert solvent. Suitable solvents for this purpose are, for example, aromatic hydrocarbons such as benzene or toluene, or halogenated hydrocarbons, such as methylene chloride, chloroform or chlorobenzene. The reaction is frequently carried out whilst adding a catalytic amount of DMF.

Process variant (b): The reaction is preferably carried out in the presence of an organic base, for example, pyridine, 4-dimethylaminopyridine, lutidine, collidine, trialkylamine, N,N-dialkylaniline, or a bicyclic, non-nucleophilic base, such as 1,4-diaza-bicyclo[2.2.2]octane (DABCO), 1,5-diazabicyclo[4.3.0]non-5-en(DBN) or 1,8-dia-zabicyclo [5.4.0]undec-7-ene (1,5-5)(DBU). The reaction is generally carried out at temperatures of −30° to +120° C., preferably from −10° to +100° C. The reaction is suitably effected in the presence of an inert solvent or solvent mixture that is free of hydroxyl groups. Suitable solvents for this purpose are, for example, aliphatic and halogenated hydrocarbons, such as chlorobenzene, methylene chloride, ethylene chloride, chloroform, carbon tetrachloride, perchloroethylene; ether and ether-like compounds, anisole, dioxane, tetrahydrofuran; nitriles such as acetonitrile, propionitrile; esters such as ethyl acetate, ethyl propionate or ethyl butyrate; ketones such as acetone, diethyl ketone, methyl ethyl ketone; compounds such as dimethyl sulphoxide (DMSO), dimethylformamide (DMF) and mixtures of such solvents with one another. However, the reaction may also take place in an excess of one of the above-mentioned bases.

In process variant (c), the reactions are expediently carried out in the presence of an inert solvent or solvent mixture at temperatures of −40° to +120° C., preferably −20° C. to +80° C. The solvents in question may be the same as those mentioned for variant (b). If required, the process is effected in the presence of a base, for example one mentioned under variant (a). In addition to the bases mentioned therein, alkali or alkaline earth metal oxides or salts may also be considered, such as sodium hydroxide, sodium carbonate, sodium or calcium hydrogen carbonate or sodium acetate.

In process variants (d) and (e), the reactions are expediently carried out in the presence of an inert solvent or solvent mixture at temperatures of −40° to +120° C., preferably 0° C. to 100° C. in the presence of a base.

The solvents and bases are the same as those listed under (b). Additional bases that may be considered are metal hydrides, such as LiH, NaH or KH.

Compounds of formula (I) obtainable according to the method or by other means may be converted in a manner known per se into other compounds of formula (I), by replacing one or more substituents of the starting compound of formula (I) in conventional manner with (an)other substituent(s) according to the invention.

Depending on the choice of appropriate reaction conditions and starting materials, it is possible to replace only one substituent with another substituent according to the invention in one reaction step, or several substituents may be replaced with other substituents according to the invention in the same reaction step.

Salts of compounds of formula (I) may be prepared in a known manner. For example, it is possible to obtain salts of compounds of formula (I) with bases, by treating the free compounds with an appropriate base or with an appropriate ion exchanger reagent.

Salts of compounds of formula (I) may be converted in conventional manner into the free compounds of formula (I), e.g. by treatment with a suitable acid or with a suitable ion exchanger reagent.

Salts of compounds of formula (I) may be transformed in known manner into other salts of a compound of formula (I).

The compounds of formula (I) in free form or in salt form may exist in the form of one of the possible isomers or as a mixture thereof, e.g. depending on the number, the absolute and relative configuration of asymmetric carbon atoms appearing in the molecule and/or depending on the configuration of non-aromatic double bonds appearing in the molecule, as pure isomers such as antipodes and/or diastereoisomers, or as isomeric mixtures such as enantiomer mixtures, e.g. racemates, diastereoisomeric mixtures or racemate mixtures. The invention relates both to the pure isomers and to all the possible mixtures of isomers, and hereinbefore and hereinafter is to be understood as such accordingly, even if the stereo-chemical details are not specifically mentioned in each case.

Depending on the choice of starting materials and methods, diastereoisomeric mixtures, racemate mixtures and mixtures of double bond isomers of compounds of formula (I) in free form or in salt form, which are obtainable by the process or in another way, may be separated in known manner, on the basis of the physical-chemical differences in their components, into the pure diastereoisomers or racemates, for example by fractiional crystallisation, distillation and/or chromatography.

Enantiomer mixtures that are obtainable correspondingly, such as racemates, may be broken down by known methods into the optical antipodes, for example by recrystallisation from an optically active solvent, by chromatography on chiral adsorbents, e.g. high pressure liquid chromatography (HPLC) on acetyl cellulose, with the assistance of suitable microorganisms, by cleavage with specific, immobilised enzymes, through the formation of inclusion compounds, e.g. using chiral crown ethers, whereby only one enantiomer is complexed, or by converting into diastereoisomeric salts and separating the diastereoisomeric mixture obtained in this way, e.g. on the basis of their different solubilities, by fractional crystallisation, into the diastereoisomers, from which the desired enantiomer can be released upon the action of suitable agents.

According to the invention, apart from isolation of corresponding isomeric mixtures, generally known methods of diastereoselective or enantioselective synthesis can also be applied to obtain pure diastereoisomers or enantiomers, e.g. by carrying out the method of the invention using educts with correspondingly suitable stereochemistry.

It is advantageous to isolate or synthesise the biologically more active isomer, e.g. enantiomer or diastereoisomer, or isomeric mixture, e.g. enantiomer mixture or diastereoisomeric mixture, provided that the individual components have differing biological efficacy.

Compounds of formula (I) in free form or in salt form can also be obtained in the form of their hydrates and/or also can include other solvents, used for example where necessary for the crystallization of compounds present in solid form.

The invention relates to all those forms of the method, according to which one starts from a compound obtainable as a primary material or an intermediate at any stage of the method and carries out all or some of the missing steps, or uses, or—especially under the reaction conditions—produces a starting material in the form of a derivative or a salt and/or its racemate or enantiomer.

In the method of the present invention, the starting materials and intermediates used, each in free form or in salt form, are preferably those that lead to the compounds of formula (I) or salts thereof described at the beginning as being especially useful.

The invention relates especially to the method of preparation described in Example P1.

The compounds of formula (I) according to the invention are active substances of preventive and/or curative merit for use in pest control and offer a very favourable spectrum of biocidal activity with favourable tolerability in warm-blooded animals, fish, and plants even at low concentrations. The active ingredients according to the invention are active against all or individual development stages of animal pests showing normal sensitivity, as well as those showing resistance, such as insects or members of the order Acarina. The insecticidal or acaricidal effect of the active substances of the invention can manifest itself directly, i.e. killing the pests either immediately or after some time has elapsed, for example when moulting occurs, or indirectly, e.g. reducing the number of eggs laid and/or the hatching rate, good efficacy corresponding to a pesticidal rate (mortality) of at least 50 to 60%.

The said animal pests include, for example, those which are mentioned in the European Patent application EP-A-736'252, page 2, line 55 to page 6, line 55. The pests mentioned therein are thus included by reference in the object of the present invention. The compounds according to the invention are also active against pests from the class of the nematodes, for example, of the families Filariidae and Setariidae and the genera Haemonchus, Trichostrongylus, Ostertagia, Nematodirus, Cooperia, Ascaris, Bunostumum, Oesophagostonum, Chabertia, Trichuris, especially Trichuris vulpis, Strongylus, Trichonema, Dictyocaulus, Capillaria, Strongyloides, Heterakis, Toxocara, especially Toxocara canis, Ascaridia, Oxyuris, Ancylostoma, especially Ancylostoma caninum, Uncinaria, Toxascaris and Parascaris; Dirofilaria, especially Dirofilaria immitis (heartworm); also especially against representatives of the genera Heterodora spp., for example Heterodera schachtii, Heterodora avenae and Heterodora trifolii; Globodera spp., for example Globodera rostochiensis; Meloidogyne spp., for example Meloidogyne incoginita and Meloidogyne javanica; Radopholus spp., for example Radopholus similis; Pratylenchus, for example Pratylenchus neglectans and Pratylenchus penetrans; Tylenchulus, for example Tylenchulus semipenetrans; Longidorus, Trichodorus, Xiphinema, Ditylenchus, Aphelenchoides and Anguina.

The active ingredients according to the invention are especially suitable for controlling sucking insects, especially of the order Homoptera, preferably for controlling these pests in vegetable, fruit, rice and cotton crops. One particular advantage of the compounds according to the invention is their systemic action.

Pests of said type which occur on plants, especially on crops and ornamentals in agriculture, horticulture and forestry, or on parts of such plants, such as fruits, blooms, leaves, stems, tubers or roots, can be controlled, i.e. kept in check or eradicated, using the active ingredients of the invention, this protection remaining for parts of some plants whose growth does not occur until later.

Target crops include especially cereals, such as wheat, barley, rye, oats, rice, corn or sorghum; beet, such as sugar beet or fodder beet; fruit, e.g. pomes, drupes and soft fruit, such as apples, pears, plums, peaches, almonds, cherries or berries, e.g. strawberries, raspberries or blackberries; leguminous plants, such as beans, lentils, peas or soybean; oleaginous fruits, such as rape, mustard, poppy, olives, sunflowers, coconut, castor oil plants, cocoa beans or groundnuts; cucumber plants, such as squashes, cucumbers or melons; fibrous plants, such as cotton, flax, hemp or jute; citrus fruits, such as oranges, lemons, grapefruit or mandarins; vegetables, such as spinach, lettuce, asparagus, cabbages, carrots, onions, tomatoes, potatoes or paprika; lauraceae, such as avocado, cinnamon or camphor; and tobacco, nuts, coffee, aubergines, sugar cane, tea, pepper, vines, hops, banana plants, natural rubber plants and ornamentals.

Other indication areas for the active ingredients of the invention are the protection of stored products and stores and of material and, in the hygiene sector, especially the protection of domestic animals and livestock against pests of said type.

The invention therefore relates also to pesticides, such as emulsifiable concentrates, suspension concentrates, ready-to-spray or ready-to-dilute solutions, coatable pastes, dilute emulsions, spray powders, soluble powders, dispersible powders, wettable powders, dusts, granulates or encapsulations in polymeric substances (chosen in accordance with the intended objectives and prevailing circumstances), comprising at least one active ingredient of the invention.

The active ingredient is used in these compositions in pure form and a solid active ingredient e.g. in a specific particle size, or preferably together with at least one of the adjuvants conventionally employed in the art of formulation, such as extenders, e.g. solvents or solid carriers, or surface-active compounds (surfactants).

The adjuvants which can be used for formulation are, for example, solid carriers, solvents, stabilizers, "slow-release" agents, dyes, and where appropriate surfactants. Carriers and adjuvants can be any substance conventionally used in crop protection agents, especially agents for slug and snail control. Adjuvants such as solvents, solid carriers, surface-active agents, non-ionic surfactants, cationic surfactants, anionic surfactants, and other adjuvants in the compositions of the invention can, for example, be the same as those described in EP-A-736'252, page 7, line 51 to page 8, line 39, and are included by reference in the object of the present invention.

As a rule, the compositions comprise 0.1 to 99%, especially 0.1 to 95%, of active ingredient and 1 to 99.9%, especially 5 to 99.9%, of at least one solid or liquid adjuvant, it being possible as a rule for 0 to 25%, especially 0.1 to 20%, of the composition to be surfactants (% in each case meaning percent by weight). Whereas concentrated compositions tend to be preferred for commercial goods, the end consumer as a rule uses dilute compositions which have substantially lower concentrations of active ingredient. Preferred compositions are composed in particular as follows (%=percent by weight):

Emulsifiable concentrates:

| | |
|---|---|
| Active ingredient: | 1 to 95%, preferably 5 to 20% |
| Surfactant: | 1 to 30%, preferably 10 to 20% |
| Solvent: | 5 to 98%, preferably 70 to 85% |

Dusts:

| | |
|---|---|
| Active ingredient: | 0.1 to 10%, preferably 0.1 to 1% |
| Solid carrier: | 99.9 to 90%, preferably 99.9 to 99% |

Suspension concentrates:

| | |
|---|---|
| Active ingredient: | 5 to 75%, preferably 10 to 50% |
| water: | 94 to 24%, preferably 88 to 30% |
| Surfactant: | 1 to 40%, preferably 2 to 30% |

Wettable powders:

| | |
|---|---|
| Active ingredient: | 0.5 to 90%, preferably 1 to 80% |
| Surfactant: | 0.5 to 20%, preferably 1 to 15% |
| Solid carrier: | 5 to 99%, preferably 15 to 98% |

Granulates:

| | |
|---|---|
| Active ingredient: | 0.5 to 30%, preferably 3 to 15% |
| Solid carrier: | 99.5 to 70%, preferably 97 to 85% |

The activity of the compositions of the invention can be substantially broadened and adapted to prevailing circumstances by adding other insecticidal substances. Additional active ingredients are, for example, substances from the following classes: organic phosphorus compounds, nitrophenols and their derivatives, formamidines, acylureas, carbamates, pyrethroids, neonicotinoides and their derivatives, pyrroles, thioureas and their derivatives, chlorinated hydrocarbons and *Bacillus thuringiensis* preparations. Especially suitable components in the mixture are azamethiphos; chlorfenvinphos; cypermethrin, cypermethrin highcis; cyromazin; diafenthiuron; diazinon; dichlorvos; dicrotophos; dicyclanil; fenoxycarb; fluazuron; furathiocarb; isazofos; iodofenphos; kinoprene; lufenuron; methacriphos; methidathion; monocrotophos; phosphamidon; profenofos; diofenolan; a substance obtainable. from the *Bacillus thuringiensis* strain GC91 or from NCTC11821; pymetrozine; bromopropylate; methoprene; disulfuton; quinalphos; tau-fluvalinate; thiocyclam; thiometon; aldicarb; azinphos-methyl; benfuracarb; bifenthrin; buprofezin; carbofuran; dibutylaminothio; cartap; chlorfluazuron; chlorpyrifos; cyfluthrin; lambda-cy-halothrin; alpha-cypermethrin; zeta-cypermethrin; deltamethrin; diflubenzuron; endosulfan; ethiofencarb; fenitrothion; fenobucarb; fenvalerate; formothion; methiocarb; heptenophos; imidacloprid; isoprocarb; methamidophos; methomyl; mevinphos; parathion; parathion-methyl; phosalone; pirimicarb; propoxur; teflubenzuron; terbufos; triazamate; abamectin; fenobucarb; tebufenozide; fipronil; beta-cyfluthrin; silafluofen; fenpyroximate; pyridaben; fenazaquin; pyriproxyfen; pyrimidifen; nitenpyram; NI-25, acetamiprid; avermectin $B_1$ (Abamectin); an insect-active extract from a plant; a preparation containing insect-active nematodes; a preparation obtainable from *Bacillus subtilis*; a preparation containing insect-active fungi; a preparation containing insect-active viruses; AC 303 630; acephat; acrinathrin; alanycarb; alphamethrin; amitraz; AZ 60541; azinphos A; azinphos M; azocyclotin; bendiocarb; bensultap; betacyfluthrin; BPMC; brofenprox; bromophos A; bufencarb; butocarboxin; butylpyridaben; cadusafos; carbaryl; carbopheno-thion; chloethocarb; chlorethoxyfos; chlormephos; cis-res-methrin; clocythrin; clofentezin; cyanophos; cycloprothrin; cyhexatin; demeton M; demeton S; demeton-S-methyl; dichlofenthion; dicliphos; diethion; dimethoat; dimethylvinphos; dioxathion; edifenphos; emamectin; esfenvalerat; ethion; ethofenprox; ethoprophos; etrimphos; fenamiphos; fenbutatinoxid; fenothiocarb; fenpropathrin; fenpyrad; fenthion; fluazinam; flucycloxuron; flucythrinat; flufenoxuron; flufenprox; fonophos; fosthiazat; fubfenprox; HCH; hexaflumuron; hexythiazox; iprobenfos; isofenphos; isoxathion; ivermectin; lambda-cy-halothrin; malathion; mecarbam; mesulfenphos; metaldehyd; metolcarb; milbemectin; moxidectin; naled; NC 184; omethoat; oxamyl; oxydemethon m; oxydeprofos; permethrin; phenthoat; phorat; phosmet; phoxim; pirimiphos M; pirimiphos A; promecarb; propaphos; prothiofos; prothoate; pyrachlophos; pyrada-phenthion; pyresmethrin; pyrethrum; RH 5992; salithion; sebufos; sulfotep; sulprofos; tebufenpyrad; tebupirimphos; tefluthrin; temephos; terbam; tetrachlorvinphos; thiacloprid; thiamethoxam; thiafenox; thiodicarb; thiofanox; thionazin; thuringiensin; tralomethrin; triarthen; triazophos; triazuron; trichlorfon; triflumuron; trimethacarb; vamidothion; xylylcarb; YI 5301/5302; zetamethrin; DPX-MP062; RH-2485; D 2341 and XMC (3,5,-xylyl methyl carbamate).

The compositions of the invention can also contain further solid or liquid adjuvants, such as stabilisers, e.g. vegetable oils, epoxidized where appropriate (e.g. epoxidized coconut oil, rapeseed oil or soya oil), antifoaming agents, e.g. silicone oil, preservatives, viscosity modulators, binders and/or tackifiers, as well as fertilisers or other active ingredients to achieve specific effects, e.g. acaricides, bactericides, fungicides, nematocides, molluscicides or selective herbicides.

The compositions of the invention are prepared in a known manner, in the absence of adjuvants, for example, by grinding, sieving, and/or compressing a solid active ingredient or active ingredient mixture, e.g. to a specific particle size, and in the presence of at least one adjuvant, for example, by intimately mixing and/or grinding the active ingredient or the mixture of active ingredients with the adjuvant(s). These methods for preparing compositions of the invention and the use of compounds I for preparing these compositions likewise form an object of the invention.

The methods of application for the compositions, i.e. the methods of controlling pests of said type, such as spraying, atomising, dusting, coating, dressing, scattering or pouring, which are chosen in accordance with the intended objectives and prevailing circumstances, and the use of the compositions for controlling pests of said type are further objects of the invention. Typical concentrations of active ingredient are between 0.1 and 1000 ppm, preferably between 0.1 and 500 ppm. The rates of application are generally 1 to 2000 g of active ingredient per hectare, especially 10 to 1000 g/ha, and preferably 20 to 600 g/ha.

A preferred method of application for crop protection is to apply the active ingredient to the foliage of the plants (leaf application), the number of applications and the rate of application depending on the intensity of infestation by the pest in question. However, the active ingredients can also penetrate the plant through the roots (systemic action) by impregnating the locus of the plant with a liquid composition, or by applying the active ingredient in solid form to the locus of the plants, e.g. the soil, for example in granular form (soil application). With paddy rice cultures, granules may be metered into the flooded paddy field.

The compositions of the invention are also suitable for protecting plant propagation material, including genetically modified propagation material, e.g. seeds, such as fruits, tubers or grains, or plant seedlings, from animal pests. The propagation material can be treated with the composition before the start of cultivation, seeds for example being dressed before they are sown. The active ingredients of the invention can also be applied to seeds (coating) by either soaking the seeds in a liquid composition or coating them with a solid composition. The composition can also be applied when the propagation material is introduced to the place of cultivation, e.g. when the seeds are sown in the seed furrow. The treatment procedures for plant propagation material and the propagation material thus treated are further objects of the invention.

The invention is illustrated by the following examples. They do not impose any limitation on the invention. The temperatures are given in degrees Celsius, and the proportions of solvents in the mixture are given as parts by volume.

PREPARATION EXAMPLES

Example P1

Preparation of 4-Trifluoromethylnicotinic Acid-N-methyl-N-methoxy-amide of Formula

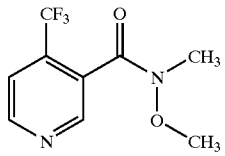

P1a): 4-Trifluoromethylnicotinic acid chloride
18.7 g of trifluoromethylnicotinic acid are mixed together with a few drops of dimethyl-formamide and heated to 85° C. At this temperature, 17.46 g of thionyl chloride are added dropwise, and afterwards stirring is effected for a further 5 hours at 85° C. Then, the excess thionyl chloride is evaporated off and the product distilled at approximately 100° C. and 40 mbar. 4-Trifluoromethylnicotinic acid chloride is obtained as a colourless oil.
P1b): 4-trifluoromethylnicotinic acid-N-methyl-N-methoxy-amide
0.61 g of N,O-dimethyl-hydroxylamine, 20 ml of water-free tetrahydrofuran, 0.05 g of 4-pyrrolidino-pyridine and 2.1 g of triethylamine are added together. The mixture is cooled to 0° C. whilst stirring, and 2.2 g of 4-trifluoromethylnicitonic acid chloride are slowly added dropwise. The reaction mass is filtered and the filtrate is evaporated totally. The residue is purified on silica gel with a mixture of hexane/ethyl acetate (35:65% parts by volume). The title compound is obtained as a colourless oil (compound 1.4).

Example P2

Preparation of 4-Trifluoromethylnicotinic Acid-N-methyl-N-(4-chloro-pyrid-2-yl)-methoxy-amide of Formula

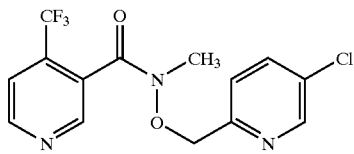

P2a): 4-Trifluoromethylnicotinic acid-N-methyl-N-hydroxy-amide
9 g of N-methyl-hydroxylamine hydrochloride, 200 ml of dichloromethane and 30 ml of triethylamine are added together. The mixture is cooled to 0° C. whilst stirring, and 15 g of 4-trifluoromethyinicitonic acid chloride are slowly added dropwise. The reaction mass is filtered and the filtrate is evaporated totally. The residue is purified on silica gel with ethyl acetate. 4-Trifluoromethylnicotinic acid-N-methyl-N-hydroxy-amide is obtained with a melting point of 99–101° C. (compound 1.3).
P2b): 4-trifluoromethylnicotinic acid-N-methyl-N-(4-chloro-pyrid-2-yl)methoxy-amide
0.5 g of 4-trifluoromethylnicotinic acid-N-methyl-N-hydroxy-amide, 10 ml of dimethyl-formamide, 0.79 g of $K_2CO_3$ and 0.55 g of 3-chloromethyl-5-chloropyridine are added together. The 4-trifluoromethyinicotinic acid-N-methyl-N-hydroxy-amide mixture is heated to 50° C. and maintained at this temperature for 4 hours whilst stirring.

The reaction mass is filtered and the residue of filtration is chromatographed on silica gel with a mixture of hexane/ethyl acetate (35:65% parts by volume). The title compound is obtained as an oil (compound 1.14).

Example P3

The remaining compounds of Tables 1 and 2 may be also prepared analogously to the methods described in P1 and P2. The melting points are given in ° C.

TABLE 1

Compounds of formula (I)

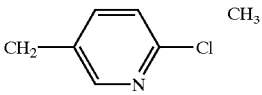

| No. | $R_1$ | $R_2$ | X | m | phys. data |
|---|---|---|---|---|---|
| 1.1 | H | H | CH | 0 | |
| 1.2 | H | $CH_3$ | CH | 0 | resin |
| 1.3 | $CH_3$ | H | CH | 0 | m.p.: 99–101 |
| 1.4 | $CH_3$ | $CH_3$ | CH | 0 | oil |
| 1.5 | $CH_2CH=CH_2$ | $CH_3$ | CH | 0 | |
| 1.6 | $CH_2C\equiv CH$ | $CH_3$ | CH | 0 | |
| 1.7 | benzyl | $CH_3$ | CH | 0 | |
| 1.8 | 4-chlorobenzyl | $CH_3$ | CH | 0 | |
| 1.9 | 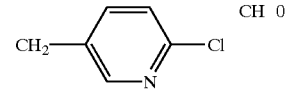 | $CH_3$ | CH | 0 | |
| 1.10 | $CH_3$ | $CH_2CH=CH_2$ | CH | 0 | oil |
| 1.11 | $CH_3$ | $CH_2C\equiv CH$ | CH | 0 | |
| 1.12 | $CH_3$ | benzyl | CH | 0 | oil |
| 1.13 | $CH_3$ | 4-chlorobenzyl | CH | 0 | resin |
| 1.14 | $CH_3$ | 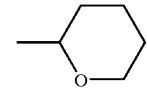 | CH | 0 | oil |
| 1.15 | 4-chlorophenyl | $CH_3$ | CH | 0 | m.p.: 66–68 |
| 1.16 | 4-chlorophenyl | $CH_2C\equiv CH$ | CH | 0 | m.p.: 124–127 |
| 1.17 | 4-chlorophenyl | $C(=O)CH_3$ | CH | 0 | resin |
| 1.18 | 4-chlorophenyl | H | CH | 0 | m.p.: 178–180 |
| 1.19 | 3,4-dichlorophenyl | $CH_3$ | CH | 0 | resin |
| 1.20 | 3,4-dichlorophenyl | $CH_2C\equiv CH$ | CH | 0 | resin |
| 1.21 | 3,4-dichlorophenyl | $C(=O)CH_3$ | CH | 0 | resin |
| 1.22 | 3,4-dichlorophenyl | H | CH | 0 | m.p.: 191–193 |
| 1.23 | n-Propyl | $CH_2CH_2C(=O)CH_3$ | CH | 0 | |
| 1.24 | $CH_3$ | 3-ethyl-benzoyl | CH | 0 | |
| 1.25 | $CH_3$ | 4-bromoenzoyl | CH | 0 | |
| 1.26 | cyclohexyl | H | CH | 0 | m.p.: 188–189 |
| 1.27 | i-propyl | H | CH | 0 | m.p.: 138–139 |
| 1.28 | benzyl | H | CH | 0 | m.p.: 180–181 |
| 1.29 | H | benzyl | CH | 0 | resin |
| 1.30 | H | $CH_2C_6F_5$ | CH | 0 | |
| 1.31 | H | 4-nitrobenzyl | CH | 0 | |
| 1.32 | H | ethyl | CH | 0 | |
| 1.33 | H | $CH_2CH=CH_2$ | CH | 0 | |
| 1.34 | H | $C(C_6H_5)_3$ | CH | 0 | |
| 1.35 | H | phenyl | CH | 0 | |
| 1.36 | H | t-butyl | CH | 0 | |
| 1.37 | H | i-butyl | CH | 0 | |
| 1.38 | H | 2,4-dinitrophenyl | CH | 0 | |
| 1.39 | H | $CH_2CH_2N(CH_3)_2$ | CH | 0 | |
| 1.40 | H | $CH_2CN$ | CH | 0 | |
| 1.41 | H |  | CH | 0 | |
| 1.42 | 3,5-dichlorophenyl | H | CH | 0 | m.p.: 174–177 |

TABLE 1-continued

Compounds of formula (I)

| No. | R₁ | R₂ | X | m | phys. data |
|---|---|---|---|---|---|
| 1.43 | 4-fluorophenyl | H | CH | 0 | m.p.: 141–143 |
| 1.44 | 4-fluorophenyl | CH₂CH≡CH | CH | 0 | m.p.: 100–102 |
| 1.45 | 4-fluorophenyl | CH₃ | CH | 0 | m.p.: 59–61 |
| 1.46 | 4-fluorophenyl | —C(=O)CH₃ | CH | 0 | m.p.: resin |
| 1.47 | 3,5-dichlorophenyl | CH₂CH≡CH | CH | 0 | m.p.: 151–154 |
| 1.48 | 3,5-dichlorophenyl | CH₃ | CH | 0 | m.p.: 86–88 |
| 1.49 | 3,5-dichlorophenyl | —C(=O)CH₃ | CH | 0 | resin |
| 1.50 | CH₃ | C₂H₅ | CH | 0 | oil |
| 1.51 | CH₃ | n-C₄H₉ | CH | 0 | oil |
| 1.52 | CH₃ | CH₂C(CH₃)₃ | CH | 0 | oil |
| 1.53 | CH₃ | n-C₁₀H₂₂ | CH | 0 | oil |
| 1.54 | CH₃ | CH₂CH₂C₆H₅ | CH | 0 | oil |
| 1.55 | CH₃ | CH₂CF₃ | CH | 0 | m.p.: 59–61 |
| 1.56 | CH₃ | CH₂C(=O)OC₂H₅ | CH | 0 | oil |
| 1.57 | H | H | N | 0 | |
| 1.58 | H | CH₃ | N | 0 | |
| 1.59 | CH₃ | H | N | 0 | |
| 1.60 | CH₃ | CH₃ | N | 0 | |
| 1.61 | CH₂CH=CH₂ | CH₃ | N | 0 | |
| 1.62 | CH₂CH≡CH | CH₃ | N | 0 | |
| 1.63 | benzyl | CH₃ | N | 0 | |
| 1.64 | 4-chlorobenzyl | CH₃ | N | 0 | |
| 1.65 | CH₂—(5-(2-chloropyridyl)) | CH₃ | N | 0 | |
| 1.66 | CH₃ | CH₂CH=CH₂ | N | 0 | |
| 1.67 | CH₃ | CH₂CH≡CH | N | 0 | |
| 1.68 | CH₃ | benzyl | N | 0 | |
| 1.69 | CH₃ | 4-chlorobenzyl | N | 0 | |
| 1.70 | CH₃ | CH₂—(5-(2-chloropyridyl)) | N | 0 | |
| 1.71 | 4-chlorophenyl | CH₃ | N | 0 | |
| 1.72 | 4-chlorophenyl | CH₂CH≡CH | N | 0 | |
| 1.73 | 4-chlorophenyl | C(=O)CH₃ | N | 0 | |
| 1.74 | 4-chlorophenyl | H | N | 0 | |
| 1.75 | 3,4-dichlorophenyl | CH₃ | N | 0 | |
| 1.76 | 3,4-dichlorophenyl | CH₂CH≡CH | N | 0 | |
| 1.77 | 3,4-dichlorophenyl | C(=O)CH₃ | N | 0 | |
| 1.78 | 3,4-dichlorophenyl | H | N | 0 | |
| 1.79 | n-propyl | CH₂CH₂C(=O)CH₃ | N | 0 | |
| 1.80 | CH₃ | 3-ethyl-benzoyl | N | 0 | |
| 1.81 | CH₃ | 4-bromobenzoyl | N | 0 | |
| 1.82 | cyclohexyl | H | N | 0 | |
| 1.83 | i-propyl | H | N | 0 | |
| 1.84 | benzyl | H | N | 0 | |
| 1.85 | H | benzyl | N | 0 | |
| 1.86 | H | CH₂C₆F₅ | N | 0 | |
| 1.87 | H | 4-nitrobenzyl | N | 0 | |
| 1.88 | H | ethyl | N | 0 | |
| 1.89 | H | CH₂CH=CH₂ | N | 0 | |
| 1.90 | H | C(C₆H₅)₃ | N | 0 | |
| 1.91 | H | phenyl | N | 0 | |
| 1.92 | H | t-butyl | N | 0 | |
| 1.93 | H | i-butyl | N | 0 | |
| 1.94 | H | 2,4-dinitrophenyl | N | 0 | |
| 1.95 | H | CH₂CH₂N(CH₃)₂ | N | 0 | |
| 1.96 | H | CH₂CN | N | 0 | |

TABLE 1-continued

Compounds of formula (I)

$$\text{structure with } CF_3, \text{ C(=O)N}(R_1)\text{OR}_2, \text{ pyridine ring with X, N, (O)}_m$$

| No. | R$_1$ | R$_2$ | X | m | phys. data |
|---|---|---|---|---|---|
| 1.97 | H | (tetrahydropyran-2-yl) | N | 0 | |
| 1.98 | 3,5-dichlorophenyl | H | N | 0 | |
| 1.99 | 4-fluorophenyl | H | N | 0 | |
| 1.100 | 4-fluorophenyl | CH$_2$CH=CH | N | 0 | |
| 1.101 | 4-fluorophenyl | CH$_3$ | N | 0 | |
| 1.102 | 4-fluorophenyl | —C(=O)CH$_3$ | N | 0 | |
| 1.103 | 3,5-dichlorophenyl | CH$_2$CH=CH | N | 0 | |
| 1.104 | 3,5-dichlorophenyl | CH$_3$ | N | 0 | |
| 1.105 | 3,5-dichlorophenyl | —C(=O)CH$_3$ | N | 0 | |
| 1.106 | CH$_3$ | C$_2$H$_5$ | N | 0 | |
| 1.107 | CH$_3$ | n-C$_4$H$_9$ | N | 0 | |
| 1.108 | CH$_3$ | CH$_2$C(CH$_3$)$_3$ | N | 0 | |
| 1.109 | CH$_3$ | n-C$_{10}$H$_{22}$ | N | 0 | |
| 1.110 | CH$_3$ | CH$_2$CH$_2$C$_6$H$_5$ | N | 0 | |
| 1.111 | CH$_3$ | CH$_2$CF$_3$ | N | 0 | |
| 1.112 | CH$_3$ | CH$_2$C(=O)OC$_2$H$_5$ | N | 0 | |

Table 2: Compounds of formula (I), wherein the combinations of R$_1$, R$_2$ and X correspond to one of lines 1.1 to 1.112 of Table 1, and m is 1.

Formulation Examples (%=Percent by Weight)

| Example F1: Emulsion concentrates | a) | b) | c) |
|---|---|---|---|
| active ingredient | 25% | 40% | 50% |
| calcium dodecylbenzenesulfonate | 5% | 8% | 6% |
| castor oil polyethylene glycol ether (36 mols EO) | 5% | — | — |
| tributyl phenol polyethylene glycol ether (30 mols EO) | — | 12% | 4% |
| cyclohexanone | — | 15% | 20% |
| xylene mixture | 65% | 25% | 20% |

Mixing of finely ground active ingredient and adjuvants results in an emulsion concentrate which is diluted with water to yield emulsions of the desired concentration.

| Example F2: Solutions | a) | b) | c) | d) |
|---|---|---|---|---|
| active ingredient | 80% | 10% | 5% | 95% |
| ethylene glycol monomethyl ether | 20% | — | — | — |
| polyethylene glycol (MW 400) | — | 70% | — | — |
| N-methylpyrrolid-2-one | — | 20% | — | — |
| epoxidised coconut oil | — | — | 1% | 5% |
| petrol (boiling limits: 160–190°) | — | — | 94% | — |

Mixing of finely ground active ingredient and adjuvants results in a solution which is suitable for application in the form of fine droplets.

| Example F3: Granulates | a) | b) | c) | d) |
|---|---|---|---|---|
| active ingredient | 5% | 10% | 8% | 21% |
| kaolin | 94% | — | 79% | 54% |
| highly dispersed silicic acid | 1% | — | 13% | 7% |
| attapulgite | — | 90% | — | 18% |

The active ingredient is dissolved in dichloromethane, the solution sprayed onto the carrier mixture, and the solvent evaporated off under vacuum.

Biological Examples

Example B1: Effect Against *Aphis raccivora*

Pea seedlings are infected with Aphis craccivora, subsequently sprayed with a spray mixture containing 400 ppm of active ingredient, and then incubated at 20° C. 3 and 6 days later, they are evaluated. The percentage reduction of the population (% response) is determined by comparing the number of dead aphids on the treated plants with those on the untreated plants.

The compounds of table 1 show good efficacy against Aphis craccivora in this test. Compounds 1.3 and 1.27 in particular show efficacy of more than 80% in this test.

Example B2: Effect Against *Myzus persicae*

Pea seedlings are infected with *Myzus persicae*, subsequently sprayed with a spray mixture containing 400 ppm of active ingredient, and then incubated at 20° C. 3 and 6 days later, they are evaluated. The percentage reduction of the population (% response) is determined by comparing the number of dead aphids on the treated plants with those on the untreated plants.

The compounds of table 1 show good efficacy against *Myzus persicae* in this test.

Example B3: Systemic Effect Against *Myzus persicae*

Pea seedlings are infected with *Myzus persicae*, then the roots are placed in a spray mixture containing 400 ppm of active ingredient, and incubated at 20° C. 3 and 6 days later, they are evaluated. The percentage reduction of the population (% response) is determined by comparing the number of dead aphids on the treated plants with those on the untreated plants.

The compounds of the tables show good efficacy against *Myzus persicae* in this test. Compounds 1.3, 1.4, 1.13, 1.22, 1.27, 1.28, 1.50, 1.52 and 1.56 in particular show efficacy of more than 80% in this test.

Example B4: Effect on *Diabrotica balteata* Larvae

Corn seedlings are sprayed with an aqueous emulsion spray mixture containing 400 ppm of active ingredient. After drying of the spray deposit, the corn seedlings are colonised with 10 second instar larvae of *Diabrotica balteata* and placed in a plastic container. Six days later they are evaluated. The percentage reduction of the population (% response) is determined by comparing the number of dead larvae on the treated plants with those on the untreated plants.

The compounds of the tables show good efficacy against *Diabrotica balteata* in this test.

Example B5: Effect on *Spodoptera littoralis* Caterpillars

Young soya plants are sprayed with an aqueous emulsion spray mixture containing 400 ppm of active ingredient. After the spray deposit has dried, the soya plants are colonised with 10 third-instar larvae of *Spodoptera littoralis* and placed in a plastic container. Three days later they are evaluated. The percentage reduction of the population and percentage reduction in feeding damage (% response) are determined by comparing the number of dead larvae and the extent of feeding damage on the treated plants with those on the untreated plants. The compounds of the tables show good efficacy against *Spodoptera littoralis* in this test.

What we claim is:
1. A compound of formula

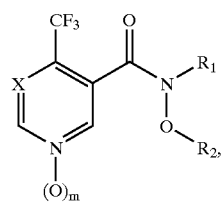

(I)

wherein
$R_1$ and $R_2$, independently of one another, are hydrogen, $C_1$–$C_6$-alkyl, $C_3$–$C_8$-cycloalkyl, $C_2$–$C_{20}$-alkenyl or $C_3$–$C_{20}$-alkinyl; or mono- or poly-substituted $C_1$–$C_{20}$-alkyl, $C_2$–$C_{20}$-alkenyl or $C_3$–$C_{20}$-alkinyl;

aryl or heterocyclyl, or aryl or heterocyclyl which are substituted by one or more substituents selected from the group consisting of $C_1$–$C_6$-alkyl, halogen-$C_1$–$C_6$-alkyl, $C_2$–$C_6$-alkenyl, $C_3$–$C_6$-alkinyl, halogen, $C_1$–$C_6$-alkoxy, halogen-$C_1$–$C_6$-alkoxy, nitro, cyano, $C_3$–$C_8$-cycloalkyl, halogen-$C_3$–$C_8$-cycloalkyl, $C_3$–$C_6$-alkenyloxy, $C_1$–$C_4$-alkylthio or di-($C_1$–$C_4$-alkyl)amine;

or —C(=O)—$R_3$;

$R_3$ is hydrogen, OH, SH, $C_1$–$C_6$-alkyl, $C_3$–$C_8$-cycloalkyl, $C_1$–$C_6$-alkoxy, $C_1$–$C_6$-alkylthio, $C_2$–$C_6$-alkenyl, $C_3$–$C_6$-alkenyloxy, $C_3$–$C_6$-alkinyl, $C_3$–$C_6$-alkinyloxy, di-($C_1$–$C_4$-alkyl)amine, aryl, heterocyclyl, aryloxy, benzyloxy or heterocyclyloxy;

$C_1$–$C_6$-alkyl, $C_3$–$C_8$-cycloalkyl, $C_1$–$C_6$-alkoxy, $C_1$–$C_6$-alkylthio, $C_3$–$C_6$-alkenyl, $C_3$–$C_6$-alkenyloxy, $C_3$–$C_6$-alkinyl or $C_3$–$C_6$-alkinyloxy, which are substituted by one or more substituents selected from the group consisting of halogen, nitro, cyano, —OH, —SH, $C_3$–$C_8$-cycloalkyl, halogen-$C_3$–$C_8$-cycloalkyl or di-($C_1$–$C_4$-alkyl)amine;

or aryl, heterocyclyl, aryloxy, benzyloxy or heterocyclyloxy, which are optionally substituted by one to three substituents selected from the group consisting of halogen, nitro, cyano, —OH, —SH, COOH, COH, $C_1$–$C_6$-alkyl, $C_1$–$C_6$-alkoxy, $C_1$–$C_6$-alkylthio, halogen-$C_1$–$C_6$-alkyl, halogen-$C_1$–$C_6$-alkoxy, halogen-$C_1$–$C_6$-alkylthio, $C_3$–$C_8$-cycloalkyl, halogen-$C_3$–$C_8$-cycloalkyl and di-($C_1$–$C_4$-alkyl)amine;

m is 0 or 1; and
X is CH or N; and
E/Z isomers, mixtures of E/Z isomers and/or tautomers thereof, in each case in free form or in salt form.

2. A compound of formula (I) according to claim 1, in free form.

3. A compound of formula (I) according to claim 1, in which X is CH.

4. A compound of formula (I) according to claim 1, in which m is 0.

5. Pesticidal composition comprising a compound according to formula (I) of claim 1 and one or more adjuvants.

6. Method of producing a composition as described in claim 5, in which the active ingredient is intimately mixed with the adjuvant or adjuvants.

7. A method for the control of pests in which an effective amount of a compound according to formula (I) of claim 1, as the active ingredient, is applied to pests or their habitat.

* * * * *